United States Patent [19]
Patel et al.

[11] Patent Number: 5,840,972
[45] Date of Patent: Nov. 24, 1998

[54] PROCESS FOR PREPARING $N^G$-MONOALKYL-L-ARGININE AND RELATED COMPOUNDS

[75] Inventors: Rajnikant Patel, Dartford; Amrik Singh Mahal, Oxon; Donald Lloyd Winston Burford, Dartford, all of United Kingdom

[73] Assignee: Glaxo Wellcome Inc., Research Triangle Park, N.C.

[21] Appl. No.: 549,795

[22] PCT Filed: May 5, 1994

[86] PCT No.: PCT/GB94/00966

§ 371 Date: Feb. 22, 1995

§ 102(e) Date: Feb. 22, 1995

[87] PCT Pub. No.: WO94/26701

PCT Pub. Date: Nov. 24, 1994

[30] Foreign Application Priority Data

May 6, 1993 [GB] United Kingdom .................. 9309321

[51] Int. Cl.$^6$ ...................... C07C 249/02; C07C 277/00; C07C 279/12
[52] U.S. Cl. .................... 562/560; 562/104; 562/118; 562/553; 562/555; 562/561; 562/575; 564/240
[58] Field of Search ..................... 562/555, 104, 562/118, 553, 560, 561, 575; 564/240

[56] References Cited

U.S. PATENT DOCUMENTS 4,656,291 4/1987 Maryanoff et al. ...................... 548/351

FOREIGN PATENT DOCUMENTS 1587258 4/1981 United Kingdom .

OTHER PUBLICATIONS

Ferrario et al., "Multigram ... Characterization", Synthetic Communications, vol. 21(1), pp. 99–105, 1991.
Maryanoff et al., A Conventional Synthesis ... Thioureas, J. Org. Chem. vol. 51, pp. 1882–1884, 1986.
Cho et al., Preparation of NG–Monoethyl–L–arginine, Anal. Biochem., vol. 139, No. 2, pp. 377–382, Jun. 1984.
Justus Liebigs Ann Chemie 722, 98–109 (1969).
546C88 for Septic Shock—Study termination Apr. 24, 1998
London Scrip Display Apr. 27, 1998 Glaxo Wellcome hits problems in sepsis.

*Primary Examiner*—Gary Geist
*Assistant Examiner*—Rosalynd Keys
*Attorney, Agent, or Firm*—Nixon & Vanderhye P.C.

[57] ABSTRACT

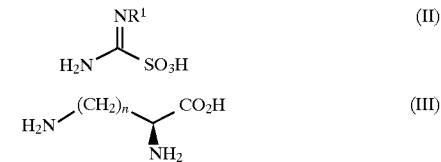

A process is disclosed for the preparation of $N^G$-monoalkyl-L-arginine and related compounds and salts thereof, for example $N^G$-monomethyl-L-arginine by reacting N-alkylaminoiminomethane sulphonic acid of formula (II) with an amino acid of formula (III).

7 Claims, No Drawings

PROCESS FOR PREPARING N$^G$-MONOALKYL-L-ARGININE AND RELATED COMPOUNDS

This is a 35 USC 371 of application PCT/GB94/00966 filed May 5, 1994.

The present invention relates to a process for the preparation of N$^G$-monoalkyl-L-arginine and related compounds and in particular N$^G$-monomethyl-L-arginine hydrochloride (L-NMMA hydrochloride).

The most widely used method for preparing guanidines in the laboratory is the reaction of amines with an S-alkyl isothiouronium salt; a method which commonly utilizes S-methylisothiouronium salts, for example the process reported by Ferrario et al. (Synth. Commun. 1991, 21, 99–105). A byproduct of this reaction is the noxious gas methyl mercaptan, which has a threshold of detection by humans of about 1ppb. Provision therefore needs to be made to convert the methyl mercaptan into an environmentally acceptable byproduct. A further disadvantage of the above process is the need to handle methyl iodide, a highly toxic substance, for the preparation of the S-methylisothiouronium salt. Whilst handling of the toxic compounds is possible on a small scale, the quantities of toxic compounds needed to be handled on a larger scale would be unacceptable.

Maryanoff et al (J. Org. Chem., 1986, 51, 1882–1884) propose a synthetic method which utilizes the intermediate aminoiminomethane sulphonic acid by the reaction of a thiourea with hydrogen peroxide. Attempts by Maryanoff et al. to repeat the oxidation procedures of Walter et al. (Liebigs Ann. Chem., 1969, 722, 98) using freshly prepared peracetic acid in methanol were unsuccessful. In addition, in order to achieve the required process using hydrogen peroxide, it was necessary to employ a catalyst, namely sodium molybdate dihydrate. The process described using hydrogen peroxide had not been used for the preparation of N$^G$-monoalkyl-L-arginine or derivatives thereof.

It has now been found that it is possible to utilize the guanylating agent N-alkylaminoiminomethane sulphonic acid, to prepare guanidine derivatives, e.g. arginine derivatives without the hazards or possibility of contamination of the catalyst in the final product associated with earlier methods.

It is the object of the present invention to provide a hazard-free process for the pure preparation of guanidine derivatives of formula (I)

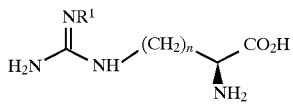

pharmaceutically acceptable salt or ester thereof wherein R$^1$ is C$_{1-6}$ alkyl and n is 3 to 5, without the problems of contamination in the final product.

Accordingly, the present invention provides a process for the preparation of a compound of formula (I) as hereinbefore defined which comprises reacting a guanylating agent of formula (II)

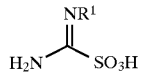

wherein R$^1$ is as hereinbefore defined, with a compound of formula (III)

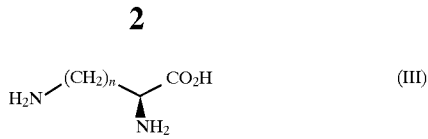

or a pharmaceutically acceptable salt or ester thereof wherein n is as hereinbefore defined.

The reaction may be carried out by the addition of an inorganic base to an aqueous solution containing compounds of formula (II) and (III), at a non-extreme temperature of from −20° C. to 100° C., for example −5° C. to 50° C. and conveniently 5° C. to room temperature. The reaction mixture is preferably at the pH of 9 to 10.

Suitably the inorganic base is potassium carbonate, sodium carbonate, sodium hydrogen carbonate, sodium hydroxide, potassium hydroxide or calcium hydroxide.

Preferably the inorganic base is calcium hydroxide, potassium carbonate or sodium hydroxide; most preferably sodium hydroxide.

Compounds of formula (II) may be prepared by the oxidation of a compound of formula (IV)

wherein R$^1$ is as hereinbefore defined.

Suitably the oxidation is effected by the reaction of a compound of formula (IV) as hereinbefore defined with peracetic acid in a polar solvent. Such solvents include water, C$_{1-6}$ alcohol or SVM (ethanol plus 2% methanol). Preferred solvents are water, methanol or SVM and most preferred is water. The reaction is preferably carried out at a non-extreme temperature of −20° C. to 100° C., for example −5° C. to 50° C. and conveniently between 0° C. to 20° C. depending upon the choice of solvent.

Whilst it may be possible to carry out the synthesis of compounds of formula (I) as a two-step synthesis, isolating the intermediate of formula (II), such a two-step synthesis is not essential. The utilization of a one-step synthesis would enable the process to be more easily adapted for use on an industrial rather than laboratory encounter.

A problem which may be encountered when carrying out the process on an industrial scale is the highly exothermic reaction of the oxidation stage encountered when using particular solvents. For this reason, it is preferred to use an aqueous solvent, e.g. water when carrying out a one-step synthesis.

The present invention includes a process for the preparation of compounds of formula (I) in the form of salts, in particular acid addition salts. Suitable salts include those formed with both organic and inorganic acids. Thus, preferred salts, include those formed from hydrochloric, hydrobromic, sulphuric, citric, tartaric, phosphonic, lactic, pyruvic, acetic, succinic, oxalic, fumaric, maleic, oxaloacetic, methanesulphonic, ethanesulphonic, p-toluenesulphonic, benzenesulphonic and isethionic acids. Preferably the salt is that formed from hydrochloric acid.

Preferred compounds of formula (I) include those wherein n is 3 or 4; i.e. arginine or lysine analogues, and in particular compounds wherein n is 3.

Preferred definitions of R$^1$ are methyl and ethyl, most preferably methyl.

Preferred compounds of formula (I) are N$^G$-monomethyl-L-arginine or the hydrochloride salt thereof.

In a further aspect the present invention provides a process for the preparation of L-NMMA hydrochloride by the reaction of L-ornithine hydrochloride and N-methylaminoiminomethane sulphonic acid.

Compounds of formula (I) and in particular L-NMMA and the hydrochloride salt thereof may be used as nitric oxide (NO) synthase inhibitors and may be of use in the treatment of conditions caused by pathological NO production for example in septic shock. Accordingly, in a further aspect of the present invention there is provided a process for the preparation of a compound of formula (I) for use as an NO synthase inhibitor, particularly for the treatment of septic shock.

The present invention will now be described by way of example only.

EXAMPLE 1

Preparation of N-methylaminoiminomethane sulphonic acid

Reagents

| | | |
|---|---|---|
| N-Methylthiourea (ALDRICH) | Fm: 90.15 | 90.0 g, ~1.0 mol |
| Peracetic acid (32% wt. in acetic acid. approximately) (FLUKA) | Fm: 76.05 | 928.0 g, 3.9 mol |
| Acetic acid | | 1000 ml |
| Methanol | | 50 ml |

To a stirred solution of peracetic acid (32% wt. in acetic acid, 928.0 g, 3.9 mol) at ~5° C., a solution of N-methylthiourea (90.0 g, 1.0 mol) in acetic acid (1000 ml) and methanol (50 ml) was added dropwise such that the reaction temperature was maintained between 10°–20° C. (ice cooling required) with stirring. Once the addition was complete, the resulting white precipitate was filtered off and dried over $P_2O_5$ at high vacuum to afford the desired product as white crystals (111.5 g, 81%).

Preparation of L-NMMA

Reagents

| | | |
|---|---|---|
| L-Ornithine hydrochloride 99% (SIGMA) | Fm: 168.15 | 25.00 g, 0.15 mol |
| N-Methylaminoiminomethane sulphonic acid | Fm: 138.15 | 17.50 g, 0.52 mol |
| Potassium carbonate anhydrous 99+% (ALDRICH) | Fm: 138.21 | 175.0 g, 1.23 mol |
| Water | | 500 ml |

To a mixture of L-ornithine hydrochloride (25.00 g, 0.15 mol) and N-methylarninoiminomethane sulphonic acid (71.50 g, 0.52 mol), water (500 ml) was added to dissolve both reagents. The mixture was stirred at room temperature for 5 minutes before potassium carbonate (175.0 g, 1.23 mol) was added in small portions (pH~10). Stirring was continued and the reaction was complete after 3 hours as judged by TLC. The reaction mixture was then concentrated under reduced pressure to dryness. To this, methanol (2×500 ml) was added and the mixture allowed to stir for 15 minutes to dissolve the L-NMMA present. The undissolved solid was filtered off and washed with copious amounts of methanol (1000 ml). The filtrate was concentrated under reduced pressure to dryness and the resulting residue was then dissolved in a small amount of water (50 ml). Hydrochloric acid (2M) (~350–400 ml) was added to the aqueous mixture to give an acidified solution (pH1–2). This solution was then poured onto the top of a bed of Dowex 50 w×8 resin (375 ml wet bed $H^+$ form) which had been pre-washed with distilled water. The resin was then washed with approximately 5.0 litres of distilled water followed by elution of the desired product using aqueous ammonia solution (1M) approximately 5.0 liters was required. The eluted fractions were concentrated under reduced pressure to afford L-NMMA free base as a light yellow foam (14.4 g, 50.9%).

L-NMMA free base (14.4 g) was dissolved in distilled water (~100 ml) and pH was adjusted to 3–4 using 2M hydrochloric acid (350 ml). The solution was stirred for 15 minutes then activated charcoal (~10.0 g) was added. The mixture allowed to stir for a further 5 minutes. The mixture was then filtered through a bed of Hyflo and the filtrate was concentrated under reduced pressure to afford L-NMMA hydrochloride (15.3 g) as a white solid. This solid was then dissolved in a refluxing mixture of SVM (225 ml) and water (25 ml) and allowed to cool at room temperature to afford pure L-NMMA hydrochloride as a fine white solid, (5.28 g, 31.4%).

EXAMPLE 2

Preparation of N-methylaminoiminomethane sulphonic acid

Reagents

| | |
|---|---|
| N-methyl thiourea (ALDRICH) | 350 g (3.9 mole) |
| SVM (solvent) | 6.3 L |
| Peracetic acid (36–40% w/v) (ALDRICH) | 2.1 L (11.6 mole) |
| SVM (solvent) | 1.3 L |
| Ammonium sulphite (35% soln) (FLUKA) | 855 ml |
| Water | 303 ml |

Method

N-Methylthiourea (350 g) was dissolved in SVM (6.3 L) with stirring. The solution was added with peracetic acid (2.1 L) as two separate streams to a vessel containing SVM (1.3 L) at 5°–10° C. (3½ hours). An initial 5% (105 ml) of the batch quantity of peracetic acid was added to ensure an excess was maintained and hence avoid partial oxidation and decomposition of the thiourea to molecular sulphur occurring. The mixture was allowed to stir for a further 2 hours and the resulting precipitate filtered, washed with SVM (5° C.) and dried under vacuum (60° C.) overnight. The white crystalline solid was obtained in 93% yield (488 g).

The reaction liquors containing excess oxidant was treated with a solution of ammonium sulphite (388 ml) with the end point being determined by a negative sodium iodide test. The above preparation was repeated affording the sulphonic acid in 92% yield.

Preparation of L-NMMA

Reagents

| | |
|---|---|
| Ornithine hydrochloride (DEGUSSA) | 500 g (2.98 mole) |
| N-methylaminoiminomethanesulphonic acid | 700 g (5.07 mole) |
| Water | 3 L |
| Sodium hydroxide (ALDRICH) | 360 g (9.00 mole) |
| Water (solvent) | 1.5 L |
| Methanol | 5 L |

L-Ornithine hydrochloride (500 g) and sulphonic acid (700 g) were dissolved in water (3 L). A solution of sodium hydroxide (360 g in 1.5 L) was added dropwise over 30 minutes. The mixture was allowed to stir for a further 2 hours maintaining the temperature between 15°–20° C. On completion, methanol was added to initiate precipitation of the inorganic salts. These were filtered and washed with methanol and the batch solution then concentrated under vacuum to remove the methanol.

Preparation of L-NMMA HCl

Reagents

| | |
|---|---|
| Dowex 50X8 H⁺ resin | 2.5 kg |
| Crude LNMMA base | 200 g |
| Hydrochloric acid (35% soln.) | |
| Aqueous ammonia solution | |

The pH of crude L-NMMA solution was adjusted to pH ¾ using 35% hydrochloric acid and divided in half The first half was loaded onto a 5 L column containing pre-water washed Dowex resin. The bound resin was then washed with water until all front running impurities were removed and a pH of 6 attained. The product was then eluted with ammonium hydroxide buffer (0.5N) and the fractions at pH10 and above were collected and monitored by HPLC. The fractions containing in excess of 50% drug content were combined and evaporated under vacuum to remove the ammonia. The pure base was acidified with hydrochloric acid (35%) to pH4 and concentrated to a residue foam. The foam was then crystallized from water (1.5 vol) and SVM (20 vol) (volume per gram of crude product) at reflux, then cooled to room temperature to effect crystallization and further cooled at 4° C. overnight. The white crystalline drug material was then filtered, washed (SVM, 5° C.) and dried under vacuum (55° C.) overnight. LNMMA Hydrochloride was obtained in a yield of 75 g with a purity of 99.1%.

EXAMPLE 3

1 Pot Preparation of L-NMMA Base

Reagents

| | |
|---|---|
| N-Methylthiourea (ALDRICH) | 200 g, (2.22 moles) |
| Peracetic Acid (ALDRICH) (36–40% wt/v) | 1.2 L, (6.66 moles) |
| Water (solvent) | 2.3 L |
| Sodium Sulphite (ALDRICH) | 300 g |
| Water (Sulphite) | 1 L |
| L-Ornithine Hydrochloride (DEGUSSA) | 195 g |
| Sodium hydroxide | 846 g (21.1 moles) |
| Water (caustic) | 2.1 L |

N-Methylthiourea (200 g) was dissolved in water (IL) with stirring. The solution was added with peracetic acid (1.2 L) as two separate streams to a vessel containing water (1.3 L) at 15°–20° C. (ca. 4 hrs). An initial 5% (60 ml) of the batch quantity of peracetic acid was added to ensure that an excess was maintained. On completion the mixture was allowed to stir for a further 2 hrs at 20° C.

The excess peracid was destroyed using aqueous sodium sulphite solution (30%, 1 L) added over a period of 1 hr at 20° C. The resultant mixture was then examined for absence of peroxide using sodium iodide indicator solution (10%).

L-Ornithine hydrochloride (195 g), was then added to the aqueous stage-1 reaction mixture and allowed to dissolve. Sodium hydroxide (846 g), dissolved in water (2.1 L), was delivered to the mixture over ca. 1 hour, maintaining the temperature between 15°–20° C. The mixture was then allowed to stir for a further 2 hrs. and on completion, methanol was added to initiate the precipitation of the inorganic salts. These were filtered and washed with methanol and the batch solution then concentrated under vacuum to remove the methanol.

Preparation of L-NMMA HCl

Reagents

| | |
|---|---|
| Dowex 50 × 8 H⁺ resin | 4 kg |
| Crude L-NMMA base | 200 g |
| Conc. Hydrochloric acid | |
| Aqueous ammonia solution | |

The pH of crude L-NMMA was adjusted to pH ¾ using conc. hydrochloric acid and divided into two. The first half was leaded onto a 4 L Column containing pre-water washed Dowex resin. The bound product was then washed and subsequently eluted as outlined for Example 2. The pure base resulting was then acidified with hydrochloric acid to pH4 and concentrated to a foam. This was crystallized from water/SVM at reflux and then cooled to room temperature at 4° C. overnight. The white crystalline product then was washed, filtered, and dried to afford L-NMMA hydrochloride in a yield of 70 g with a purity of 98.6%.

We claim:

1. A process for the preparation of a compound of formula (I)

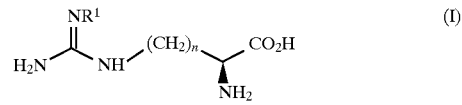

or a pharmaceutically acceptable salt or ester thereof wherein $R^1$ is $C_{1-6}$ alkyl and n is 3 to 5, which comprises reacting a guanylating agent of formula (II)

wherein $R^1$ is as hereinbefore defined, with a compound of formula (III)

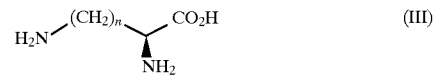

or a pharmaceutically acceptable salt or ester thereof wherein n is as hereinbefore defined, in the presence of an inorganic base.

2. A process according to claim 1, for the preparation of a compound of formula (I) or a pharmaceutically acceptable salt or ester thereof in which n is 3 or 4.

3. A process according to claim 2, for the preparation of a compound of formula (I) or a pharmaceutically acceptable salt or ester thereof in which n is 3.

4. A process according to claim 1, for the preparation of a compound of formula (I) or a pharmaceutically acceptable salt or ester thereof in which $R^1$ is methyl or ethyl.

5. A process according to claim 4, for the preparation of a compound of formula (I) or a pharmaceutically acceptable salt or ester thereof in which $R^1$ is methyl.

6. A process according to claim 1 for the preparation of $N^G$-monomethyl-L-arginine or the hydrochloride salt thereof.

7. A process for the preparation of a compound of formula (I)

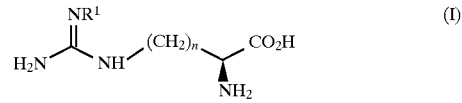

wherein $R^1$ and n are as hereinbefore defined, which comprises the oxidation of a compound of formula (IV)

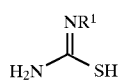 (IV)
wherein the oxidising agent is peracetic acid and thereafter, in the presence of an inorganic base, the reaction with a compound of formula (III)
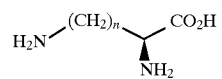 (III)
wherein n is as hereinbefore defined, the process being carried out without isolation of any intermediate products.
* * * * *